(12) United States Patent
Lipiecki et al.

(10) Patent No.: US 7,919,638 B2
(45) Date of Patent: *Apr. 5, 2011

(54) METHOD OF PREPARING ORGANOMETALLIC COMPOUNDS

(75) Inventors: Francis Joseph Lipiecki, Haddonfield, NJ (US); Stephen G. Maroldo, Ambler, PA (US); Deodatta Vinayak Shenai-Khatkhate, Danvers, MA (US); Robert A. Ware, Wellesley, MA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/701,518

(22) Filed: Feb. 5, 2010

(65) Prior Publication Data

US 2010/0185003 A1    Jul. 22, 2010

Related U.S. Application Data

(63) Continuation of application No. 12/215,828, filed on Jun. 30, 2008, now Pat. No. 7,659,414.

(60) Provisional application No. 60/961,370, filed on Jul. 20, 2007.

(51) Int. Cl.
*C07F 5/00*     (2006.01)
*C07F 7/00*     (2006.01)
(52) U.S. Cl. ............... 556/1; 556/95; 556/103; 556/187
(58) Field of Classification Search ............... 556/1, 95, 556/103, 187
See application file for complete search history.

(56) References Cited

U.S. PATENT DOCUMENTS

| 6,495,707 | B1 | 12/2002 | Leese et al. |
| 6,537,506 | B1 | 3/2003 | Schwalbe et al. |
| 7,659,414 | B2 * | 2/2010 | Lipiecki et al. ............... 556/1 |
| 2003/0100792 | A1 | 5/2003 | Koch et al. |
| 2004/0254389 | A1 | 12/2004 | Odedra et al. |

FOREIGN PATENT DOCUMENTS

WO     WO 01/23328     9/2000

OTHER PUBLICATIONS

V. Hessel and H. Lowe., "Microchemical Engineering", Chemical and Engineering Technology, 26(1); 13-24 (2003) and 26(4), 391-408 (2003).
V. Hessel, P. Lob and H. Lowe, Development of Microstructured Reactors to Enable Organic Synthesis Rather than Subduing Chemistry, Current Organic Chemistry, 9, 765-787 (2005).
V. Hessel and H. Lowe "Organic Synthesis with Microstructured Reactors", Chemical and Engineering Technology, 28(3), 267-284 (2005).
T. Schwalbe, A. Kursawe, J. Sommer, Chemical and Engineering Technology, 28(4), 408-419 (2005).

* cited by examiner

*Primary Examiner* — Porfirio Nazario Gonzalez
(74) *Attorney, Agent, or Firm* — Tifiani M. Cottingham

(57) ABSTRACT

A method of preparing an ultra-pure metal amidinate compound comprising using a microchannel device for synthesis in reacting a metal halide solution with a lithium amidinate solution to produce an ultra-pure alkylmetal compound for processes such as chemical vapor deposition.

12 Claims, No Drawings

METHOD OF PREPARING ORGANOMETALLIC COMPOUNDS

This application claims the benefit of priority under 35 U.S.C. §119(e) of U.S. Provisional Patent Application No. 60/961,370 filed on Jul. 20, 2007 and Non-Provisional patent application Ser. No. 12/215,828 filed on Jun. 30, 2008.

This invention relates to methods of making organometallic compounds (OMCs). In particular the invention is directed to methods of making organometallic compounds of high purity for processes such as chemical vapor deposition.

Metal films may be deposited on surfaces, such as non-conductive (Electronic materials applications) surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), chemical beam epitaxy ("CBE") and atomic layer deposition ("ALD"). Chemical vapor deposition processes, such as metalorganic chemical vapor deposition ("MOCVD"), deposit a metal layer by decomposing organometallic precursor compounds at elevated temperatures, i.e., above room temperature, either at atmospheric pressure or at reduced pressures. A wide variety of metals may be deposited using such CVD or MOCVD processes.

For semiconductor and electronic device applications, organometallic precursor compounds must be ultra pure and be substantially free of detectable levels of both metallic impurities, such as silicon and zinc, as well as other impurities including hydrocarbons and oxygenated compounds. Ideally, ultra purity is producing materials with level of impurities <0.1 wt %, preferably <1 ppm, or even <1 ppb. Oxygenated impurities are typically present from the solvents used to prepare such organometallic compounds, and are also present from other adventitious sources of moisture or oxygen. Achieving ultra purity is important when manufacturing materials for electronic applications including Group III and V OMCs for CVD to produce compound semi-conductors for LEDs and optoelectronic devices, or organometallic precursors for ALD to grow thin films for advanced silicon chips. Some impurities have similar boiling points in relation to the organometallic precursor compounds making it difficult to achieve high purity with conventional distillation technology.

Much work has been done to improve the synthetic methods for making ultra-pure organometallic precursor compounds. Historically, organometallic precursor compounds have been prepared by batch processes but recently, as disclosed in U.S. Pat. No. 6,495,707 and U.S. Patent Publication No. 2004/0254389, continuous methods for producing organometallic compounds such as trimethylindium and trimethylgallium have become available.

Despite these advances, the synthesis of organometallic compounds remains difficult. Many of the reactions are exothermic and the production of large amounts, particularly with such high purity, is difficult. In addition it is difficult to scale the production of materials to match fluctuating demand and storage of the organometallic compounds can be undesirable as impurities and degradation products can be introduced.

Traditional methods used for purification include distillation, crystallization, adduct purification, mass-selective ultra-centrifuge, and chemical treatment combined with distillation. While these methods provide some reduction in the level of impurities, there is a continuing need to produce ultra-pure organometallic compounds to meet the performance demands of today's most advanced electronic devices. Furthermore, there is often an economic constraint to the purity levels attainable with existing methods. Excessive capital or operating costs can limit the attainable purity due to unacceptable yield loss, energy input, or process cycle time due to the physical and/or chemical properties of the impurities and the organometallic compound.

For example, it is possible to estimate the minimum number of equilibrium stages required for distillation based on the relative volatility (a) of the components and the desired purity using the Fenske Equation. To remove the most problematic, near boiling impurities (a<1.2), the number of stages, or height equivalent theoretical plates (HETP), can exceed 50, 100, or even 200 which can require a column height of >10 meters even with today's most advanced packings (HETP=0.05 to 0.20 m). A column of this size poses difficult scale-up and operability challenges and safety concerns from the large inventory of pyrophoric organometallic compounds, when attempting to make ultra-pure materials.

Accordingly, there is an ongoing need for new methods of preparing ultra-pure organometallic compounds for use as CVD precursors.

The present invention meets this foregoing need by drawing upon the benefits of microchannel devices. Microchannel devices provide better control of process conditions, improved safety, and speed to market from laboratory development to commercial manufacturing. A continuous flow micro-reactor, one example of a microchannel device, helps achieve improved synthesis yields and purity through superior heat and mass transfer to control the reaction conditions and minimize the risk of a reaction runaway or hazardous spill through low inventory of materials. The microchannel device further enables production scale-up by "numbering-up" multiple devices to meet market demand with no performance loss and at significant time and cost savings without the need for traditional process scale-up studies.

Microchannel devices can also be used for separation and purification steps of reagents, solvents, intermediates, or final products with similar benefits. The basis for the benefits in microchannel technology arise from the high surface area provided in the device which enables high exchange rates between phases. Enhancement of separation is achieved in the microchannel architecture dimensions, typically 1 to 1000 microns, through an increased importance of interfacial phenomena and reduced distances for heat and mass-transfer. The superior heat and mass transfer in these devices provides high exchange rates between phases and better temperature control for more efficient separation stages or lower height equivalent theoretical plate (HETP). This enables more stages for higher purity in a fixed separation device geometry. There are also benefits in lower capital intensity and lower operating costs through improved energy efficiency by better integration of heat exchange.

Microchannel devices can be used in a wide range of separation applications including distillation, adsorption, extraction, absorption, and gas stripping.

By drawing upon the benefits of microchannel technology, the present invention succeeds in producing ultra-pure organometallic precursor compounds.

In one aspect of the present invention there is provided a process for preparing organometallic metal alkyl compound compounds of ultra-high purity comprising:
reacting a metal halide solution and an alkylmetal solution in a microchannel device to yield a metal alkyl compound wherein the resulting compound has the minimum purity required for chemical vapor deposition processes.

In a second aspect of the present invention there is provided a method of preparing a metal alkyl compound of ultra-high purity comprising purifying an organometallic compound comprising impurities in a microchannel device to reduce the level of impurities with relative volatility (a) between 0.8<a <1.5 to a level useful in electronic materials applications.

As used herein, the term "metal halide" refers to a compound containing a metal and at least one halogen bound to the metal. The metal may also have additional, non-halide substituents.

As used herein, the term "electronic materials applications" refers to applications including but not limited to chemical vapor deposition ("CVD"), physical vapor deposition ("PVD"), and other epitaxial techniques such as liquid phase epitaxy ("LPE"), molecular beam epitaxy ("MBE"), chemical beam epitaxy ("CBE") and atomic layer deposition ("ALD"). In electronic materials applications, the level of impurities with relative volatility (a) between 0.8<a <1.5 typically must be below 100 ppm, alternatively below 1 ppm.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Likewise, "alkenyl" and "alkynyl" include linear, branched and cyclic alkenyl and alkynyl, respectively. The term "Group IV metal" is not intended to include Group IV non-metals such as carbon. Likewise, the term "Group VI metal" is not intended to include Group VI non-metals such as oxygen and sulfur. "Aryl" refers to any aromatic moiety, and preferably an aromatic hydrocarbon.

The articles "a" and "an" refer to the singular and the plural.

As used herein, "CVD" is intended to include all forms of chemical vapor deposition for example: Metal Organic Chemical Vapor Deposition (MOCVD), Metal Organic Vapor Phase Epitaxy (MOVPE), Oganometallic Vapor Phase Epitaxy (OMVPE), Organometallic Chemical Vapor Deposition (OMCVD) and Remote Plasma Chemical Vapor Deposition (RPCVD). In CVD processes organometallic compounds must have a purity of at least 99.9999% in order to meet stringent electrical or optoelectronic performance requirements of semiconducting devices produced using these organometallic compounds.

Unless otherwise noted, all amounts are percent by weight and all ratios are molar ratios. All numerical ranges are inclusive and combinable in any order except where it is clear that such numerical ranges are constrained to add up to 100%.

Microchannel devices offer novel opportunities in chemical synthesis and purification. Microchannel devices have channel cross-section dimensions (widths) of 0.1 to 5,000 micrometers, preferably 1 to 1,000 micrometers, or more preferably, 1 to 100 micrometers. Microchannel devices are typically comprised of multiple channels for fluid flow in parallel to the primary flow direction. Due to the small channel cross-section dimensions, the microchannel device has a high surface area to volume ratio resulting in highly efficient mass and heat transfer. In particular, mass transfer is on the molecular scale and heat transfer coefficients can be up to 25 kilowatts/square meterKelvin or more. For comparison, heat transfer coefficients of conventional jacketed reactors are typically 0.1 to 0.2 kilowatts/square meterKelvin. The highly efficient mass and heat transfer in a microchannel device permits much tighter control of reaction conditions such as temperature, reactant concentration and residence time. Temperature control is particularly important for preparation of high purity organometallic products. Deviations from isothermal conditions for exothermic or endothermic reactions can lead to increased amounts of undesired side products resulting in lower product yield and purity. Precise temperature control in the production of high purity products decreases or, in some cases eliminates, the need for subsequent purification, thus decreasing the overall amount of resources required to produce the organometallic compound.

As each microchannel device typically produces a small quantity of organometallic precursor, a number of microchannel devices may be used in parallel. Total volume produced by the series of microchannel devices can be controlled by increasing or decreasing the number of microchannel devices in use at any given point in time, thus decreasing or eliminating the need for product storage.

Microchannel devices may be made from any conventional material including but not limited to metals, polymers, ceramics, silicon or glass. Exemplary metals include but are not limited to metal alloys, such as Hastelloy™ alloys, readily available from Haynes International, Inc., and austenitic stainless steels such as, for example, 304, 312, and 316 stainless steels. Methods of fabrication include but are not limited to mechanical micro-machining, molding, tape casting, etching, laser patterning, sandblasting, hot embossing, lithography, and micro-stereolithography. The microchannel device may be constructed with both smooth channel walls and/or channels with structural features on the channel walls that enhance heat and mass transfer. A microreactor is one example of a microchannel device.

In some microchannel device embodiments used for conducting reactions, the microreactor comprises an inlet for each reagent. In reactions employing three or more reagents, two or more reagents may be combined and fed to the microreactor via a single inlet with the proviso that the total number of reagents is not combined until in the microreaction zone. For example, when the reaction employs three reagents, two of the reagents may be co-fed to the microreactor via the same inlet and the third reagent may be fed via a second inlet.

The microchannel device can comprise a separate channel system for temperature control via an external cooling or heating source. Exemplary systems include, but are not limited to hot oil, hot water, hot steam, cold oil, cold water, cold baths, and refrigeration units. As used herein, by "hot" is meant temperatures above room temperature, typically above 35° C. As used herein, by "cold" is meant temperatures below room temperature, typically below 15° C. In the case of a microreactor, the device is operated at a temperature appropriate for the particular synthesis reactions.

The microchannel device may further comprise a micromixer for mixing of the inlet streams.

The microchannel device can have a length ranging from 1 micrometer to 1 meter, or greater, depending on the process requirements or the device fabrication method. Multiple microchannel devices can be used sequentially if required to achieved the desired overall length. In the case of a microreactor, the length of the microchannel device is dictated by the kinetics of the particular reaction being performed in addition to the flow rate and temperature. Slower reactions require a longer residence time in the microreactor and hence a longer microreactor. Additionally, when sequential reactions are desired the microreactor can comprise additional inlets along the length of the device or between devices for additional reagents.

The microchannel device comprises an outlet for the removal of product. In some embodiments the microchannel device comprises two outlets, one for a liquid stream and one for a gaseous stream. The product streams from a microreactor may then be subjected to purification, using either conventional purification methods, microchannel purification, or a combination thereof.

An example of a microreactor is disclosed in U.S. Pat. No. 6,537,506 which describes a stacked plate, multichannel reactor incorporating heat transfer fluid pathways, reactant fluid pathways, product pathways, mixing chambers and reaction chambers.

The microchannel device may optionally contain a wick or membrane structure to control the liquid film thickness and enhance interfacial phenomena. Microchannel devices may be used for fluid separation including distillation. The application of microchannel devices to a commercially important distillation application is the $C_2$ splitter, which separates ethane from ethylene. The microchannel distillation process can reduce energy consumption and capital costs for ethylene production.

The present invention provides a process for preparing an organometallic compound by reacting a metal salt with an alkylating agent in a microchannel device to produce an ultra-pure alkylmetal compound for processes such as chemical vapor deposition. Additionally the alkylating agents of the present invention may themselves be purified.

Examples of metal salt and alkylating agent combinations include but are not limited to reacting a metal halide with a trialkylaluminum solution, a metal halide solution with an alkyl magnesium halide, or a metal halide solution with an alkyl lithium solution in a microchannel device, such as a microreactor, to produce an alkyl metal compound. In some embodiments the molar ratio of alkylating agent to metal salt is greater than or equal to one. In some embodiments the molar ratio is greater than or equal to 2. In some embodiments the molar ratio is greater than or equal to 3.

The metal halide may comprise a Group II, Group III, Group IV, or Group V metal. There are a sufficient number of halogens present in the metal halide to form a neutral compound. Exemplary metal halides include, but are not limited to, $ZnCl_2$, $GaCl_3$, $InCl_3$, $InBr_3$, $InI_3$, $GeCl_4$, $SiCl_4$, $SnCl_4$, $PCl_3$, $AsCl_3$, $SbCl_3$ and $BiCl_3$.

The trialkylaluminum solution comprises three alkyl groups, which may be the same or different. Each alkyl group comprises 1 to 8 carbons. The alkyl groups may be straight chain, branched or cyclic. The alkyl magnesium halide and alkyl lithium compounds comprise a single alkyl group comprising 1 to 8 carbons. Likewise, the alkyl groups may be straight chain, branched or cyclic.

The metal salt solution and the alkylating agent solution may comprise any organic solvent which is inert to the reaction between the two constituents and is also inert to any products resulting from the reaction. In some embodiments the metal salt solution is free of solvent, i.e., the metal salt is already in liquid form and is added "neat". The solvent should be chosen to provide sufficient solubility for the reaction to proceed. The metal salt solution and the alkylating agent solution may use the same or different solvents. Particularly suitable organic solvents include, but are not limited to, hydrocarbons and aromatic hydrocarbons. Exemplary organic solvents include, without limitation, benzene; alkyl substituted benzenes such as toluene, xylene, and $(C_4$-$C_{20})$ alkyl benzenes such as $(C_{10}$-$C_{12})$alkyl benzenes and $(C_{10}$-$C_{20})$alkyl biphenyls; and aliphatic hydrocarbons such as pentane, hexane, heptane, octane, decane, dodecane, squalane, cyclopentane, cyclohexane, and cycloheptane; and mixtures thereof. More preferably, the organic solvent is benzene, toluene, xylene, $(C_4$-$C_{20})$alkyl benzenes, hexane, heptane, cyclopentane or cyclohexane. It will be appreciated that more than one organic solvent may be advantageously used. Such organic solvents are generally commercially available from a variety of sources, such as Aldrich Chemicals (Milwaukee, Wis.). Such solvents may be used as is or, preferably, purified prior to use.

Preferably, such organic solvents are dry and deoxygenated prior to use. The solvents may be deoxygenated by a variety of means, such as purging with an inert gas, degassing the solvent in vacuo, or a combination thereof. Suitable inert gases include argon, nitrogen and helium, and preferably argon or nitrogen.

In an alternative embodiment, ionic liquids will be employed as the solvents that do not interact with organometallic synthesis under consideration, and offer "green solvents" that are environment-friendly. Ionic liquids are generally salts that are liquid at low temperatures, having melting points under 100° C. Many ionic liquids remain in the liquid phase at room temperature, and are referred to as room temperature ionic liquids. Ionic liquids are composed entirely of ions and typically they are composed of bulky organic cations and inorganic anions. Due to the high Coulombic forces in these compounds, ionic liquids have practically no vapor pressure.

Any suitable ionic liquid may be employed in the present invention. Exemplary cations used in ionic liquids include, but are not limited to, hydrocarbylammonium cations, hydrocarbylphosphonium cations, hydrocarbylpyridinium cations, and dihydrocarbylimidazolium cations. Exemplary anions useful in the present ionic liquids include, but are not limited to, chlorometalate anions, fluoroborate anions such as tetrafluoroborate anions and hydrocarbyl substituted fluoroborate anions, and fluorophosphate anions such as hexafluorophosphate anions and a hydrocarbyl substituted fluorophosphate anions. Examples of chlorometalate anions include, but are not limited to, chloroaluminate anion such as tetrachloroaluminate anion and a chlorotrialkylaluminate anion, chlorogallate anions such as chlorotrimethylgallate and tetrachlorogallate, chloroindate anions such as tetrachloroindate and chlorotrimethylindate.

Suitable chloroaluminate-based ionic liquids include, without limitation, those having a hydrocarbyl substituted ammonium halide, a hydrocarbyl substituted phosphonium halide, a hydrocarbyl substituted pyridinium halide, or a hydrocarbyl substituted imidazolium halide. Exemplary chloroaluminate-based ionic liquids include, but are not limited to, trimethylphenyl ammonium chloroaluminate ("TM-PACA"), benzyltrimethyl ammonium chloroaluminate ("BT-MACA"), benzyltriethyl ammonium chloroaluminate ("BTEACA"), benzyltributyl ammonium chloroaluminate ("BTBACA"), trimethylphenyl phosphonium chloroaluminate ("TMPPCA"), benzyltrimethyl phosphonium chloroaluminate ("BTMPCA"), benzyltriethyl phosphonium chloroaluminate ("BTEPCA"), benzyltributyl phosphonium chloroaluminate ("BTBPCA"), 1-butyl-4-methyl-pyridinium chloroaluminate ("BMPYCA"), 1-butyl-pyridinium chloroaluminate ("BPYCA"), 3-methyl-1-propyl-pyridinium chloroaluminate ("MPPYCA"), 1-butyl-3-methyl-imidazolium chloroaluminate ("BMIMCA"), 1-ethyl-3-methyl-imidazolium chloroaluminate ("EMIMCA"), 1-ethyl-3-methyl-imidazolium bromo-trichloroaluminate ("EMIMBTCA"), 1-hexyl-3-methyl-imidazolium chloroaluminate ("HMIMCA"), benzyltrimethyl ammonium chlorotrimethylaluminate ("BTMACTMA"), and 1-methyl-3-octyl-imidazolium chloroaluminate ("MOIMCA").

Other suitable ionic liquids include those having a fluoroborate anion or a fluorophosphate anion, such as, but not limited to, trimethylphenyl ammonium fluoroborate ("TM-PAFB"), benzyltrimethyl ammonium fluoroborate ("BT-MAFB"), benzyltriethyl ammonium fluoroborate ("BTEAFB"), benzyltributyl ammonium fluoroborate ("BT-BAFB"), trimethylphenyl phosphonium fluoroborate ("TMPPFB"), benzyltrimethyl phosphonium fluoroborate ("BTMPFB"), benzyltriethyl phosphonium fluoroborate ("BTEPFB"), benzyltributyl phosphonium fluoroborate ("BTBPFB"), 1-butyl-4-methyl-pyridinium fluoroborate ("BMPFB"), 1-butyl-pyridinium fluoroborate ("BPFB"), 3-methyl-1-propyl-pyridinium fluoroborate ("MPPFB"), 1-butyl-3-methyl-imidazolium fluoroborate ("BMIMFB"), 1-ethyl-3-methyl-imidazolium fluoroborate ("EMIMFB"), 1-ethyl-3-methyl-imidazolium bromo-trifluoroborate ("EMIMBTFB"), 1-hexyl-3-methyl-imidazolium fluoroborate ("HMIMFB"), 1-methyl-3-octyl-imidazolium fluoroborate ("MOIMFB"), and benzyltrimethyl ammonium fluorophosphate ("BTMAFP").

Ionic liquids are generally commercially available or may be prepared by methods known in the art. These compounds may be used as is or may be further purified.

The concentration and amounts of the solutions are chosen such that the molar ratio of the alkylating agent compound to the metal salt is greater than or equal to the stoichiometric requirement for the particular alkylation reaction.

The metal halide with a trialkylaluminum solution reaction may be performed at −10 to 100° C. Useful pressures are 1 to 10 bar.

The metal halide solution with an alkyl magnesium halide or an alkyl lithium solution reaction may be performed at −50 to 50° C. Useful pressures are 1 to 10 bar.

In another embodiment of the present invention, there is provided a method to prepare metal amidinate compounds that are useful sources suitable for Atomic Layer Deposition (ALD). The metal amidinate composition is an organometallic compound suitable for use as an ALD precursor having the formula $(R^1NCR^2NR^3)_nM^{+m}L^1_{(m-n)}L^2_p$, wherein $R^1$, $R^2$ and $R^3$ are independently chosen from H, $(C_1-C_6)$alkyl, $(C_2-C_6)$alkenyl, $(C_2-C_6)$alkynyl, dialkylamino, di(silyl-substituted alkyl)amino, disilylamino, di(alkyl-substituted silyl)amino, and aryl; M=a metal; $L^1$=an anionic ligand; $L^2$=a neutral ligand; m=the valence of M; n=0-6; p=0-3; and wherein m≧n. Metal amidinates can be homoleptic or heteroleptic in nature, i.e. may comprise of different amidinate ligands or a combination of amidinates and other anioinic ligands. Such compounds are suitable in a variety of vapor deposition methods, such as chemical vapor deposition ("CVD"), and are particularly suitable for atomic layer deposition ("ALD"). Also provided is a composition including the above described compound and an organic solvent. Such a composition is particularly suitable for use in ALD and direct liquid injection ("DLI") processes.

The method of preparing an organometallic amidinate compound comprises reacting a metal halide solution with an amidinato lithium solution in a microchannel device such as a microreactor to produce a metal alkylamidinate compound, wherein the molar ratio of amidinatolithium compound to metal halide is greater than or equal to one. In some embodiments the molar ratio is greater than or equal to 2. In some embodiments the molar ratio is greater than or equal to 3.

The metal halide may comprise a Group II through Group VIII metal. There are a sufficient number of halogens present in the metal halide to form a neutral compound. Exemplary metal halides include $ZnCl_2$, $GaCl_3$, $InBr_3$, $AlCl_3$, $HfCl_4$, $ZrCl_4$, $GeCl_4$, $SiCl_4$, $TaCl_5$, $WCl_6$, $SbCl_3$ and $RuCl_3$.

The amidinatolithium compound comprises a single amidinato group comprising alkyl or aryl or cyclic groups with 1 to 8 carbons. The alkyl groups may be straight chain, branched, or cyclic.

The metal halide solution and the amidinatolithium solution may comprise any solvent which is inert to the reaction between the metal halide and the amidinato lithium solution and is also inert to any products resulting from the reaction. The solvents and reagents need to be dry, and deoxygenated. The solvent should be chosen to provide sufficient solubility for the reaction to proceed. The metal halide solution and the amidinato lithium solution may use the same or different solvents. Exemplary solvents include, but are not limited to the aforementioned list.

In some embodiments the metal halide solution is free of solvent, i.e., the metal halide is already in liquid form and is added "neat". The concentration and amounts of the solutions is chosen such that the molar ratio of the amidinato lithium compound to the metal halide is greater than or equal to the stoichiometric ratio required for the desired reaction.

The reaction may be performed at −50 to 50° C. Useful pressures are 1 to 10 bar.

In yet another embodiment, a method of preparing an organometallic compound comprises, reacting a metal halide solution with an alkyl metal solution in the presence of a tertiary amine, a tertiary phosphine, or a mixture of a tertiary amine and a tertiary phosphine in a microchannel device such as a microreactor.

In particular the method comprises reacting a metal halide of the formula $R_mMX_{4-m}$ with a Group III compound of the formula $R^4_nM^1X^1_{3-n}$ in the presence of a tertiary amine or a tertiary phosphine or mixtures of a tertiary amine and a tertiary phosphine in an organic solvent to provide an alkylmetal compound, wherein each R is independently chosen from H, alkyl, alkenyl, alkynyl and aryl; M is chosen from a Group IV metal and a Group VI metal; each X is independently a halogen; each $R^4$ is independently chosen from $(C_1-C_6)$alkyl; $M^1$ is a Group III metal; each $X^1$ is independently a halogen; m=0-3; and n=1-3. The Group IV metal halides and the Group VI metal halides are generally commercially available, such as from Gelest, Inc. (Tullytown, Pa.), or may be prepared by methods known in the literature. Such compounds may be used as is or may be purified prior to use. It will be appreciated by those skilled in the art that more than one metal halide, more than one Group III compound, and combinations thereof may be used.

Exemplary Group IV metals include, but are not limited to, silicon, germanium and tin. Exemplary Group VI metals include, without limitation, tellurium and selenium. M is preferably silicon, germanium or tin and more preferably germanium. X may be any halogen. Each X may be the same or different. In one embodiment, m=0. When m=0, a Group IV or Group VI metal tetrahalide is used. In other embodiments, m may be 1, 2 or 3.

A wide variety of alkyl, alkenyl and alkynyl groups may be used for R. Suitable alkyl groups include, without limitation, $(C_1-C_{12})$alkyl, typically $(C_1-C_6)$alkyl and more typically $(C_1-C_4)$alkyl. In one embodiment, the alkyl groups are bulky alkyl groups. By "bulky alkyl group" is meant any sterically hindered alkyl group. Such bulky alkyl groups have at least three carbons, there being no particular upper limit to the number of carbons in such group. It is preferred that the bulky alkyl groups each have from three to six carbon atoms, and more preferably three to five carbon atoms. Such bulky alkyl groups are preferably not linear, and are preferably cyclic or branched. Exemplary alkyl groups include methyl, ethyl, n-propyl, iso-propyl, n-butyl, iso-butyl, sec-butyl, tert-butyl, pentyl, cyclopentyl, hexyl, and cyclohexyl. More typically, suitable alkyl groups include ethyl, iso-propyl, and tert-butyl. Suitable alkenyl groups include, without limitation, $(C_2-C_{12})$alkenyl, typically $(C_2-C_6)$alkenyl and more typically $(C_2-C_4)$alkenyl. Exemplary alkenyl groups include vinyl, allyl, methallyl and crotyl. Typical alkynyl groups include, without limitation, $(C_2-C_{12})$alkynyl, typically $(C_2-C_6)$alkynyl and more typically $(C_2-C_4)$alkynyl. Suitable aryl groups are $(C_6-$ $C_{10}$)aryl, including, but not limited to, phenyl, tolyl, xylyl, benzyl and phenethyl. When two or more alkyl, alkenyl or alkynyl groups are present, such groups may be the same or different.

Any of the above alkyl, alkenyl, alkynyl or aryl groups of R may optionally be substituted, such as with halogen or dialkylamino. By "substituted" it is meant that one or more hydrogens on the alkyl, alkenyl, alkynyl or aryl group are replaced with one or more halogens or dialkylamino groups.

A wide variety of Group III compounds may be used. Suitable Group III compounds useful in the present invention typically have the formula $R^4{}_nM^1X^1{}_{3-n}$, wherein each $R^4$ is independently selected from $(C_1$-$C_6)$alkyl; $M^1$ is a Group IIIA metal; $X^1$ is halogen; and n is an integer from 1 to 3. $M^1$ is suitably boron, aluminum, gallium, indium and thallium, and preferably aluminum. Preferably, $X^1$ is selected from fluorine, chlorine or bromine. Suitable alkyl groups for $R^4$ include, but are not limited to, methyl, ethyl, n-propyl, iso-propyl, n-butyl, iso-butyl, and tert-butyl. Preferred alkyls include, methyl, ethyl, n-propyl and iso-propyl. In one embodiment, n is 3. Such Group III compounds where n is 3 include trialkylboron, trialkylaluminum, trialkylgallium, trialkylindium and trialkylthallium, with trialkylaluminum compounds being preferred. In an alternate embodiment, n is 1 or 2. Such Group IIIA compounds where n is 1-2 include dialkylaluminum halides such as dialkylaluminum chlorides. Group III compounds are generally available commercially from a variety of sources, such as Gelest, or may be prepared by a variety of methods known in the literature. Such compounds may be used as is or may be purified prior to use.

Suitable tertiary amines include, but are not limited to, those having the general formula $NR^5R^6R^7$, wherein $R^5$, $R^6$ and $R^7$ are independently selected from $(C_1$-$C_6)$alkyl, di($C_1$-$C_6$)alkylamino-substituted $(C_1$-$C_6)$alkyl, and phenyl and wherein $R^5$ and $R^6$ may be taken together along with the nitrogen to which they are attached to form a 5-7 membered heterocyclic ring. Such heterocyclic ring may be aromatic or non-aromatic. Particularly suitable tertiary amines include, but are not limited to, trimethylamine, triethylamine, tri-n-propylamine, tri-n-butylamine, tri-iso-propylamine, tri-iso-butylamine, dimethylaminocyclohexane, diethylaminocyclohexane, dimethylaminocyclopentane, diethylaminocyclopentane, N-methylpyrrolidine, N-ethylpyrrolidine, N-n-propylpyrrolidine, N-iso-propylpyrrolidine, N-methylpiperidine, N-ethylpiperidine, N-n-propylpiperidine, N-iso-propylpiperidine, N,N'-dimethylpiperazine, N,N'-diethylpiperazine, N,N'-dipropylpiperazine, N,N,N', N'-tetramethyl-1,2-diaminoethane, pyridine, pyrazine, pyrimidine, and mixtures thereof. Preferred amines include trimethylamine, triethylamine, tri-n-propylamine, triisopropylamine, and tri-n-butylamine. In one embodiment, the tertiary amine is triethylamine or tri-n-propylamine.

Exemplary tertiary phosphines include, without limitation, those of the general formula $R^8R^9R^{10}P$, where $R^8$, $R^9$, and $R^{10}$ are independently chosen from $(C_1$-$C_6)$alkyl, phenyl and $(C_1$-$C_6)$alkyl-substituted phenyl. Suitable tertiary phosphines include triethyl phosphine, tripropyl phosphine, tributyl phosphine, phenyl dimethyl phosphine, phenyl diethyl phosphine and butyl diethyl phosphine.

It will be appreciated by those skilled in the art that more than one tertiary amine or tertiary phosphine may be used. Mixtures of a tertiary amine and a tertiary phosphine may also be used. Such tertiary amines and tertiary phosphines are generally commercially available from a variety of sources. Such tertiary amines and tertiary phosphines may be used as is or, preferably further purified prior to use.

A wide variety of organic solvents may be used. Typically, such organic solvents do not contain oxygenated species such as ether linkages, and are preferably free of oxygen. Exemplary organic solvents include, but are not limited to, hydrocarbons and aromatic hydrocarbons. Suitable organic solvents include, without limitation, benzene, toluene, xylene, pentane, hexane, heptane, octane, decane, dodecane, squalane, cyclopentane, cyclohexane, cycloheptane, and mixtures thereof. It will be appreciated that more than one organic solvent may be advantageously used in the present invention. In an alternative embodiment, the tertiary amine may be used as the organic solvent. Such organic solvents are generally commercially available from a variety of sources, such as Aldrich Chemicals (Milwaukee, Wis.). Such solvents may be used as is or, preferably, purified prior to use.

Preferably, such organic solvents are deoxygenated prior to use. The solvents may be deoxygenated by a variety of means, such as purging with an inert gas, degassing the solvent in vacuo, or a combination thereof. Suitable inert gases include argon, nitrogen and helium, and preferably argon or nitrogen.

The specific tertiary amine, tertiary phosphine and organic solvent used depend upon the particular alkylmetal compound desired. For example, the organic solvent and tertiary amine may be selected such that they are more volatile or less volatile than the desired alkylmetal compound. Such differences in volatility provide easier separation of the alkylmetal compound from both the amine and organic solvent. The selection of the tertiary amine and the organic solvent are well within the abilities of those skilled in the art.

In general, the tertiary amine and/or tertiary phosphine is present in a stoichiometric amount to the Group IIIA compound. The mole ratio of the metal halide to the Group IIIA compound may vary over a wide range, such as from 1:0.1 to 1:5, the particular mole ratio being dependent upon the alkylmetal compound desired. Another suitable range of mole ratios is from 1:0.5 to 1:2. Mole ratios greater than 1:5 are also expected to be effective.

The particular alkylmetal compound obtained from the present method can be controlled by selection of the mole ratio of the metal halide and the Group IIIA compound, i.e. the number of halogens replaced in the metal halide compound can be controlled by the number of moles of Group III compound. For example, in the reaction of a Group IV metal tetrahalide (A), such as germanium tetrachloride, with a trialkylaluminum (B), such as trimethylaluminum, a mole ratio of 1:0.5 (A:B) provides an alkyl Group IV metal trihalide; a mole ratio of 1:1 (A:B) provides a dialkyl Group IV metal dihalide; a mole ratio of 1:1.5 (A:B) provides a trialkyl Group IV metal halide; and a mole ratio of 1:2 (A:B) provides a tetraalkyl Group IV metal. Thus, one, two, three or four halogens of the metal halide compound may be replaced according to the present method.

In one embodiment, the Group III compound, tertiary amine and/or tertiary phosphine and organic solvent may be combined in any order prior to reaction with the metal halide. In a further embodiment, the Group III compound is first combined with the tertiary amine and/or tertiary phosphine to form an amine-Group III adduct or a phosphine-Group III adduct. Typically, the amine-Group III adduct may be formed at a wide variety of temperatures. Suitable temperatures for forming the adduct are from ambient to 90° C. The metal halide is then reacted with the amine-Group III adduct to form the desired alkylmetal compound. It is preferred that the metal halide is added dropwise, either neat or as a hydrocarbon solution, to the amine-Group III adduct. Alternatively, the amine-Group III adduct may be added dropwise to the metal halide, either neat or as a hydrocarbon solution. Suitable temperatures to form the alkylmetal compound are from ambient to 80° C. Thus, in one embodiment, the present invention provides a method for preparing alkylmetal compounds comprising reacting a Group III compound with a tertiary amine to form an amine-Group III adduct in an organic solvent that is free of oxygenated species; and reacting the amine-Group III adduct with a Group IV metal halide, Group VIA metal halide or a mixture thereof in the organic solvent. When a tertiary phosphine is used in the above reactions, a phosphine-Group III adduct is formed.

In another embodiment, the metal halide may be combined with the Group III compound and optionally an organic solvent prior to mixing with the tertiary amine and/or tertiary phosphine. The tertiary amine and/or tertiary phosphine and optionally an organic solvent may then be combined with the metal halide-Group IIIA compound mixture using suitable mixing zones within the microchannel device or conventional external agitation techniques. Alternatively, the metal halide-Group III compound may be added to the tertiary amine and/or tertiary phosphine and optionally an organic solvent. While not intending to be bound by theory, it is believed that the transalkylation reaction does not begin until the metal halide, Group III compound and tertiary amine are combined.

Alternatively, the alkylmetal compound may be prepared in a continuous manner. For example, the metal halide and the Group III compound may be independently added in a continuous manner to a microchannel reactor and contacted with a tertiary amine and/or tertiary phosphine in a suitable solvent, such as an aromatic or aliphatic hydrocarbon. The addition of the metal halide and the Group III compound can be controlled by a variety of suitable means, such as by the use of mass flow controllers. In such a continuous process, the desired alkylmetal compound may be recovered, such as by distillation, while the metal halide and Group III compound are being added to the reaction zone. In a further alternative, a mixture of the metal halide and the Group III compound may be combined with the tertiary amine and/or tertiary phosphine in a suitable solvent. In such a continuous process, the desired alkylmetal compound may be recovered, such as by distillation, while the metal halide/Group III compound mixture is being added to the reaction zone.

The organometallic compounds may be used as is or suitably purified by a variety of techniques, such as by distillation, sublimation, and recrystallization. The present method provides organometallic compounds that are substantially free of metallic impurities such as aluminum, gallium, indium, cadmium, mercury and zinc. The organometallic compounds are also substantially free of oxygenated impurities such as ethereal solvents, and preferably free of such oxygenated impurities. By "substantially free" it is meant that the present compounds contain less than 0.5 ppm of such impurities. The present organometallic compounds have a purity of at least 99.99% or alternatively 99.9999% by weight. Specifically, the organometallic compounds of the present invention comprise impurity levels by weight of less than 100 ppm to less than 1 ppm.

Organometallic compounds with ultra-high purity for electronic materials applications can be further purified using microchannel devices. The microchannel device can be used to purify the reactants, intermediates, or final products or combinations thereof to achieve ultra-high high purity compounds for electronic applications. The organometallic compounds can be produced in microchannel reactors as described above, or in traditional reactors including batch stirred tanks, semi-batch, continuous flow stirred tanks, continuous flow tubular reactors, reactive distillation reactors, and other known methods. Ultra-high purity material for electronic applications is often difficult to achieve via conventional thermal separation methods such as distillation and sublimation, or by mass transfer separation methods such as extraction, absorption and adsorption due to low concentration driving forces.

Organometallic compounds containing impurities with near boiling points (relative volatility, $0.8<a<1.5$, where a=the vapor pressure of the impurity/vapor pressure of desired pure compound) are especially difficult to purify via staged distillation processes with conventional packing. The column may require a large number of stages, >50, >100, sometimes >200, or high reflux ratios, >10, >20, sometimes >50, or both, which adds to the investment and operating cost and complexity of the process. The microchannel device provides an improved solution to these problems. The small channel dimensions generate higher transport gradients to intensify heat and mass transfer, and increased surface to volume provides higher effective exchange area in a fixed geometry. Both factors contribute to more efficient separation (smaller Height Equivalent Theoretical Plate, HETP) for purification, especially beneficial for attaining high purity.

Ultra high purity organometallic compounds can also be produced in a microchannel device by adsorptive or chemical purification technique such as adduct-purification. A selective adsorbent or adduct-forming Lewis base such as an amine, phosphine, or ether can be supported on microchannel surfaces, providing very high exchange area to contact the impurity-containing stream. Other microchannels can be provided for flow of heat transfer fluid for precise temperature control of the device to efficiently regulate and cycle between the adsorption and desorption steps.

Separation processes, such as distillation, stripping, extraction, and adsorption, based on microchannel technology provide the enhanced heat and mass transfer required to achieve ultra pure products (ppm, ppb). These separation processes additionally provide the intensification of transfer stages needed to solve the problem of separating fluid mixtures with similar boiling points (relative volatility, $0.8<a<1.5$) to high purity levels. Advantageous operating conditions include temperatures and pressures where one or more of the fluid components is in the liquid phase and capable of undergoing a phase change either to the vapor state or to an adsorbed state on a sorbent. This can include temperatures from $-25°$ C. to $250°$ C., and pressures from 0.1 Pa to 10 MPa. Feed impurity levels can range from 1 ppm up to 10 wt % or even 50 wt % of the fluid mixture.

The organometallic compounds of the present invention are particularly suitable for use as precursors in all vapor deposition methods such as LPE, MBE, CBE, ALD, CVD, MOCVD and MOVPE. The present compounds are useful for depositing films containing one or more of Group IV, Group VI or both Group IV and Group VI metals. Such films are useful in the manufacture of electronic devices, such as, but not limited to, integrated circuits, optoelectronic devices and light emitting diodes.

Films of Group IV and/or Group VI metals are typically deposited by first placing the desired alkylmetal compound, i.e. source compound or precursor compound, in a delivery device, such as a cylinder, having an outlet connected to a deposition chamber. A wide variety of cylinders may be used, depending upon the particular deposition apparatus used. When the precursor compound is a solid, the cylinders disclosed in U.S. Pat. No. 6,444,038 (Rangarajan et al.) and U.S. Pat. No. 6,607,785 (Timmons et al.), as well as other designs, may be used. For liquid precursor compounds, the cylinders disclosed in U.S. Pat. No. 4,506,815 (Melas et al.) and U.S. Pat. No. 5,755,885 (Mikoshiba et al.) may be used, as well as other liquid precursor cylinders. The source compound is maintained in the cylinder as a liquid or solid. Solid source compounds are typically vaporized or sublimed prior to transportation to the deposition chamber.

The source compound is typically transported to the deposition chamber by passing a carrier gas through the cylinder. Suitable carrier gasses include nitrogen, hydrogen, and mixtures thereof. In general, the carrier gas is introduced below the surface of the source compound, and passes up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The deposition chamber temperature is from 200 to 1200° C., the exact temperature selected being optimized to provide efficient deposition. Optionally, the temperature in the deposition chamber as a whole can be reduced if the substrate is maintained at an elevated temperature, or if other energy such as radio frequency ("RF") energy is generated by an RF source.

Suitable substrates for deposition, in the case of electronic device manufacture, may be silicon, gallium arsenide, indium phosphide, and the like. Such substrates may contain one or more additional layers of materials, such as, but not limited to, dielectric layers and conductive layers such as metals. Such substrates are particularly useful in the manufacture of integrated circuits, opotoelectronic devices and light emitting diodes.

Deposition is continued for as long as desired to produce a film having the desired properties. Typically, the film thickness will be from several hundred angstroms to several tens of nanometers to several hundreds of microns or more when deposition is stopped.

The following examples are expected to further illustrate various aspects of the present invention, but are not intended to limit the scope of the invention in any aspect. All manipulations are performed in an inert atmosphere, typically under an atmosphere of dry nitrogen.

EXAMPLES

Comparative Example #1

Tetramethylgermane was synthesized according to the following equation:

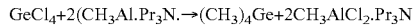

$GeCl_4 + 2(CH_3Al.Pr_3N. \rightarrow (CH_3)_4Ge + 2CH_3AlCl_2.Pr_3N$

To 150 g of high boiling linear alkylbenzenes was added under nitrogen trimethylaluminum (40 g, 0.554 moles) in a 3-necked round-bottomed flask. To this was added n-propylamine (79.5 g, 0.554 moles) dropwise at room temperature. The addition lasted 30 minutes during which period the mixture became warm (ca. 50° C.). After the addition was complete and the mixture was allowed to cool to room temperature, neat germanium chloride (40 g, 0.186 moles) was added dropwise at room temperature to the adduct formed. The addition took 1 hour during which time the reaction mixture warmed again to ca. 60° C. After cooling to room temperature, the reaction mass was heated to 160 to 170° C. (oil bath temperature) during which time 20 g of crude product, tetramethylgermane, distilled through a U-tube into a dry ice cooled receiver. The identity of the product was confirmed by $^1$H nmr ($\equiv$CH$_3$ resonance at 0.1 ppm) and showed it to contain some tripropyl amine (<5%). Yield of crude product was 81.6%. $^1$H nmr analysis of the remaining pot residues indicated the presence of more tetramethylgermane that was not isolated.

Example 1

Tetramethylgermane is synthesized according to the following equation.

$GeCl_4 + 2(CH_3)_3AlPr_3N(CH_3)_4Ge + 2CH_3AlCl_2Pr_3N$

An equimolar solution of trimethylaluminum and n-propylamine is made in a high boiling linear alkylbenzenes solvent under nitrogen. The trimethylaluminum/n-propylamine solution and neat germanium chloride are added continuously at room temperature to the microchannel device. The microchannel device provides separate flow paths for the reagents and the said flow paths communicate with each other in a mixing region in which the reagents contact each other, The reagent flows are controlled to maintain a molar ratio of trimethylaluminum to germanium chloride of 3. The mixture enters a reaction region in the microchannel device leading to alkylation occurring between the reagents. The said reaction region has a width perpendicular to the direction of flow in the range of 1 to 100 micrometers. The said reaction region has a length (in the direction of the flow) in the range 1 micrometer to 1 meter, the optimum length to be determined by the kinetics of the alkylation reaction to achieve an adequate residence time (1 second to 10 minutes) that is set by adjusting the flow rates and to offer at least 80% conversion. The temperature of the reaction is controlled to within +/−1° C. by the flow of a heat transfer fluid, such as Therminol, in separate flow channels to the reaction channels within the microchannel device. The reaction product stream exits the microchannel reactor and is collected and distilled at 160-170° C. to yield the desired Me$_4$Ge product. The purity of the Me$_4$Ge product as measured by FT-NMR and ICP-AES is expected to be 99.9999% pure.

Example 2

High purity trimethylaluminum-tripropylamine adduct was synthesized using microchannel device according to the following equation.

$(CH_3)_3Al + Pr_3N(CH_3)_3Al.Pr_3N$ Adduct

The microchannel reactor comprising multiple, parallel channels constructed of 316 SS with cross-sectional dimensions of approximately 1×3 mm and length greater than 1 m was used in preparation of purified organoaluminum—tertiary amine adduct. Each channel of microchannel device was in contact with heat exchange zones. A feedstream of trimethylaluminum (TMA) at room temperature containing 31.6 ppm Si (as detected by ICP technique) was fed to the continuous flow reactor at 2.5 kg/hr. A feedstream of tripropylamine at room temperature was co-fed to the reactor through a separate injection port at 5.0 kg/hr. The two feeds were internally mixed in the flow channels. Reactor temperature was controlled using cooling oil (40° C.) circulated to the reactor heat exchange channels to maintain a steady process outlet temperature of ~50° C. The reactor effluent (7.5 kg/hr) was fed to a continuous thin film evaporator to purify the adduct. The evaporator surface was continuously wiped by a rotating blade and operated at 2 torr and a jacket temperature of 80° C. The purified TMA:Adduct was collected in greater than 98 wt % yield and sampled for analysis. The ICP analysis showed the product to have significantly reduced silicon impurity than the starting material, as shown by Si=0.7 ppm reduced from 31.6 ppm.

What is claimed is:

1. A process for preparing organometallic metal alkyl compounds of ultra-high purity comprising:
   reacting a metal halide solution and an alkylmetal solution in a microchannel device to yield a metal alkyl compound wherein the resulting compound has the minimum purity required for chemical vapor deposition processes.

2. The process of claim 1 wherein the purity of the compound is at least 99.99% pure.

3. The process of claim 1 wherein the metal halide comprises at least one metal selected from the group consisting of Group II, Group III, Group IV and Group V.

4. The process of claim 3 wherein the metal halide comprises: $ZnCl_2$, $GaCl_3$, $InCl_3$, $InBr_3$, $InI_3$, $GeCl_4$, $SiCl_4$, $SnCl_4$, $PCl_3$, $AsCl_3$, $SbCl_3$ and $BiCl_3$.

5. The process of claim 1 wherein the alkylmetal solution comprises:
   trialkylaluminum, organomagnesium halide, and organolithium.

6. The process of claim 5 further wherein the reaction is performed in the presence of a tertiary amine, a tertiary phosphine, or a mixture of a tertiary amine and a tertiary phosphine.

7. The process of claim 1 further comprising purifying the alkyl metal solution.

8. The process of claim 5 wherein the alkyl metal solution is further purified using a microchannel device.

9. A method of preparing a metal alkyl compound of ultra-high purity comprising: purifying an organometallic compound comprising impurities in a microchannel device to reduce the level of impurities with relative volatility (a) between $0.8<a<1.5$ to a level useful in electronic materials applications.

10. The method of claim 9 comprising purifying a metal alkyl compound comprising impurities in a microchannel device to reduce the level of impurities with relative volatility (a) between $0.8<a<1.5$ to less than 1 ppm.

11. The method of claim 9 comprising purifying a metal alkyl compound comprising impurities in a microchannel device using temperature swing adsorption to reduce the level of impurities via adduct formation.

12. The method of claim 9 wherein the microchannel device further comprises a height equivalent theoretical plate (HETP) of less than 5 cm.

* * * * *